United States Patent [19]

Frische et al.

[11] Patent Number: 5,302,670

[45] Date of Patent: Apr. 12, 1994

[54] NEW PLASTICS ON FATTY ACID BASIS

[75] Inventors: Rainer Frische, Frankfurt am Main; Jürgen Volkheimer, Wiesbaden; Klaus Wollmann, Eschhofen; Herrmann Schomann, Langen; Judith Schneider; Alexander Ach, both of Frankfurt am Main; Renate Gross-Lannert, Dietzenbach; Bernd Best, Moerfelden, all of Fed. Rep. of Germany

[73] Assignee: Battelle-Institut e.V., Frankfurt, Fed. Rep. of Germany

[21] Appl. No.: 659,317

[22] PCT Filed: Jun. 22, 1990

[86] PCT No.: PCT/EP90/00995

§ 371 Date: Feb. 28, 1991

§ 102(e) Date: Feb. 28, 1991

[87] PCT Pub. No.: WO91/00305

PCT Pub. Date: Jan. 10, 1991

[30] Foreign Application Priority Data

Jun. 29, 1989 [DE] Fed. Rep. of Germany ....... 3921305

[51] Int. Cl.$^5$ .............................................. C08L 67/08
[52] U.S. Cl. .................. 525/444.5; 528/272; 528/274; 528/288; 528/293; 528/295.5; 528/299; 528/302; 528/303; 528/306; 528/307; 528/313; 528/314; 528/332; 528/335; 528/336; 528/337; 528/392; 528/422; 525/437; 525/440; 525/444; 525/447; 524/742; 524/745; 524/755
[58] Field of Search ............... 528/272, 274, 288, 293, 528/295.5, 299, 302, 303, 306, 307, 313, 314, 332, 335, 336, 337, 392, 422; 525/437, 440, 444, 444.5, 447; 524/742, 745, 755

[56] References Cited

U.S. PATENT DOCUMENTS

| 2,844,609 | 7/1958 | Tesoro . | |
| 3,001,958 | 9/1961 | Schwarcman | 528/81 |
| 3,045,034 | 1/1958 | Zankl et al. | 554/106 |
| 3,388,100 | 6/1968 | Thoma et al. | 528/60 |
| 3,574,691 | 4/1971 | Stolpa et al. | 560/125 |
| 4,190,564 | 2/1980 | Tominaga et al. | 523/415 |
| 4,535,142 | 8/1985 | Brauer et al. | 528/75 |

FOREIGN PATENT DOCUMENTS

| 21471 | 1/1981 | European Pat. Off. . |
| 1049575 | 1/1959 | Fed. Rep. of Germany . |
| 1495251 | 1/1969 | Fed. Rep. of Germany . |
| 67117 | 4/1972 | Fed. Rep. of Germany . |
| 2434147 | 2/1975 | Fed. Rep. of Germany . |
| 2559698 | 7/1977 | Fed. Rep. of Germany . |
| 2114744 | 10/1979 | Fed. Rep. of Germany . |
| 209190 | 4/1984 | Fed. Rep. of Germany . |
| 23668 | of 1910 | United Kingdom . |
| 558854 | 1/1944 | United Kingdom . |
| 632242 | 11/1949 | United Kingdom . |
| 1084981 | 9/1967 | United Kingdom . |
| 1153557 | 5/1969 | United Kingdom . |

OTHER PUBLICATIONS

C. K. Lyons et al., "New Castor Oil-Based Urethane Elastomers", *Journal of the American Oil Chemists Society*, vol. 50, pp. 112-114 (1973).

(List continued on next page.)

*Primary Examiner*—John Kight, III
*Assistant Examiner*—Sam A. Acquah
*Attorney, Agent, or Firm*—Spencer, Frank & Schneider

[57] ABSTRACT

The present invention relates to plastics that can be obtained by reacting unsaturated and/or hydroxyl-group-containing fatty acids or their esters or mixtures of various such fatty acids and esters with bifunctional ester-forming and/or amide-forming compounds and, if necessary, subsequently converting ethylenic double bonds, to give difatty acid diamides, difatty acid diesters, difatty acid amide esters, monofatty acid amide amines or monofatty acid amide alcohols as monomer components which contain at least two reactive groups suited for linkage to give polymers, in particular ethylenic double bonds, hydroxyl groups, epoxy groups or amino groups, and by linking the said compounds in the known way via a second group of bifunctional compounds that are capable of reacting with these free reactive groups to give the desired plastics.

15 Claims, No Drawings

OTHER PUBLICATIONS

B. Gruber et al., "Polyols on the Basis of Oleochemical Raw Materials", *Fat Science Technology,* vol. 89, pp. 147–151 (1987).

Prof. Dr.-Ing. E.h Dr. Richard Vieweg et al., "Polyurethane" Kunststoff-Handbuch, Band VII, pp. 73, 208, 514 (1986).

Chemical Abstracts, vol. 80, Abstract No. 135205t (1974).

Derwent, CPI, No. 835B/01 (1978).

Derwent, CPI, No. 87-141183/20 (1986).

Abstract No. 48459U-DE (1969).

James F. Brower et al., "Decomposition of Aminophylline in Suppository Formulations", Journal of American Sciences, vol. 69, No. 8, pp. 942–944 (Aug. 1980).

Juan Cornejo et al., "Oxidative Degradation of Hydrocortisone in Presence of Attapulgite", American Pharmaceutical Association, vol. 69, No. 8, p. 945 (Aug. 1980).

Von H.-W. Eckert "Kondensationsprodukte aus β-Hydroxy-äthyläthylendiamin . . . ", Fette, Seifen & Anstrichmittel Nr. 9, pp. 527–533 (1972).

Chemical Abstracts, Abstract No. 221447q, vol. 95 (1981).

Chemical Abstracts, Abstract No. 206453g, vol. 108, (1988).

Chemical Abstracts, Abstract No. 193804a, vol. 101, (1984).

NEW PLASTICS ON FATTY ACID BASIS

CROSS REFERENCE TO RELATED APPLICATIONS

This application is related to German Application No. P 3921306.4, filed Jun. 29, 1989, and International Application No. PCT/EP90/00995, filed Jun. 22, 1990.

BACKGROUND OF THE INVENTION

1. Field of the Invention

The present invention relates to a new group of plastics based on fatty acids that can be obtained from natural oils and fats.

2. Technology Review

Natural oils and fats serve not only as initial substances for producing a multitude of technically important basic materials; under certain conditions, they can also be used to a substantially increased extent to produce polymers, in particular plastics. At present, the production of polymers from fats and oils is based essentially on three different possibilities.

The first possibility makes use of the, observation that polyunsaturated fats and fatty acids tend to polymerize when heated or exposed to atmospheric oxygen. These properties are of importance, for example, in the production of linoleum and in the curing of lacquers and varnishes (oil paints) as well as of sealing compounds, e.g., glazier's putty. The field of application in this case is naturally limited to oils with a high content of polyunsaturated fatty acids, so-called drying oils such as linseed oil, wood oil or nut oil.

A second possibility is to use oils and fats which, because of their composition, predominantly contain two or more alcohol groups per triglyceride molecule, and to process them with appropriate reactive compounds, e.g. diisocyanates, to give polymeric structures. Suitable substances for such reactions are, for example, castor oil or hydrogenated castor oil, which can be used directly as triglycerides. However, the range of application of this method is also limited by the available oils and fats and, in addition, the direct use of triglycerides normally permits only such polymers to be produced that are cross-linked and therefore cannot be processed thermoplastically.

The third possibility is to break down the fatty acids contained in oils and fats into diactive fatty acid splitting products such as dicarboxylic acids by splitting reactions, e.g. ozonolysis, the reactive groups, for example, carboxylic acid groups, being attached to both ends of the hydrocarbon chains. According to this method, it is possible to produce azelaic acid from oleic acid on an industrial scale. The dicarboxylic acids can then be reacted with diamines to give polyamides or with diols to give polyesters. It is also common practice in the chemical industry to split ricinoleic acid (from castor oil), react one of the splitting products to give 11-amino-undecanoic acid and polycondensate the latter to give nylon R 11 (Rilsan). Although thermoplastic polymers as well can be produced via these or other diactive fatty acid splitting products, this method also has decisive drawbacks. On the one hand, splitting the fatty acids into diactive products is relatively complicated an(i involves major losses, and on the other hand considerable amounts of various by-products are formed, especially aliphatic monocarboxylic acids, the chain length of which is less interesting from the technical point of view, and the subsequent purifying operations are therefore difficult.

The above examples already show the basic interest of the plastics industry in using natural fats and oils.

SUMMARY OF THE INVENTION

The invention provides for a thermoplastic material produced by the process of (a) reacting unsaturated hydroxyl-group-containing fatty acids or their esters or mixtures of various such fatty acids and esters with bifunctional ester-or amide-forming compounds; (b) subsequently reacting, if desired, any existing ethylenic double bonds, to yield difatty acid diamides, difatty acid diesters, difatty acid amide esters, monofatty acid amide amines or monofatty acid amide alcohols as monomer components which contain at least two functional groups suited for the production of polymers in particular ethylenic double bones, hydroxyl groups, epoxy groups or amino groups; and, (c) linking said monomers via a second group of bifunctional compounds that are capable of reacting with the said functional groups to produce a plastic material.

DETAILED DESCRIPTION OF THE INVENTION

An object of the present invention was to make accessible in an advanced manner the fatty acids which are contained especially in natural fats and oils and have functional groups such as double bonds or hydroxyl functions, and which are suitable for the reaction to give polymers, and to extend in this way the range of application of fats and oils in the plastics industry. The present invention was based on the idea that molecules with at least two reactive groups, e.g. double bonds, epoxy groups or hydroxyl groups, can be reacted with other appropriate bifunctional compounds, e.g. diisocyanates, to give linear polymers. It must be ensured that two reactive groups react per each monomer. If fewer groups per molecule react, chain termination occurs; reaction of more than two groups per molecule results in cross-linking.

The subject matter of the present invention thus is fatty-acid-based plastics produced by the process of (a) reacting unsaturated hydroxyl-group-containing fatty acids or their esters or mixtures of various such fatty acids and esters with bifunctional ester-or amide-forming compounds; (b) subsequently reacting, if desired, any existing ethylenic double bonds, to yield difatty acid diamides, difatty acid diesters, difatty acid amide esters, monofatty acid amide amines or monofatty acid amide alcohols as monomer components which contain at least two functional groups suited for the production of polymers, in particular ethylenic double bones, hydroxyl groups, epoxy groups or amino groups; and, (c) linking said monomers via a second group of bifunctional compounds that are capable of reacting with the said functional groups to produce a plastic material.

Producing plastics according to the invention requires unsaturated and/or amino- and/or hydroxyl-group-containing fatty acids, preferably with chain lengths of 10 to 24 carbon atoms, or their derivatives such as esters. As a rule, natural fats and oils will be used as initial substances, which have a particularly high content of such a fatty acid, e.g. oleic acid, linoleic acid, linolenic acid or ricinoleic acid. If these fats and oils contain fatty acids with one or several double bonds, the hydroxyl or amino groups can also be obtained subsequently, the hydroxyl groups, for example, by oxidising the initial substance with peracetic acid or performic acid, whereby the range of fatty acids for further reaction can be significantly extended. Oils that are particularly well suited for the method according to the invention are, for example, the oil from the seeds of Euphorbia lathyris, olive oil, linseed oil, castor oil and hydrogenated castor oil, sunflower oil that is rich in linoleic acid or oleic acid, in particular sunflower oil of the "high-oleic" species, rapeseed oil, especially of the high-erucic-acid species, the oil of Jatropha curcas or the oils of marine animals, e.g. fish or whale oil.

The initial substance is directly reacted with the bifunctional ester-forming or amide-forming substances. Appropriate bifunctional compounds include diols, diamines and amino alcohols. Instead of the diols, it is also possible to use the corresponding thio compounds in which one or both OH groups have been substituted by SH groups. For the reaction with diols, it is recommended to use the initial substance in pre-purified form. As described in the simultaneously filed Patent Application (Attorney Docket BATEL 0027), using crude oils and fats for the reaction with diamines or amino alcohols does not present any problems either.

Diols that can be used in the method according to the invention are, for example, primary and secondary aliphatic, cyclo-aliphatic, aliphatic-aromatic and aromatic diols, preferably with 2 to 44 carbon atoms. Preferably used substances are 2-butyne-1,4-diol, 2-butene-1, 4-diol, 1,5-pentanediol, 1,6-hexanediol, neopentyl glycol, N,N-diethylaminopropanediol-2,3 or hydroxypivalic acid neopentyl glycol ester. Particularly preferred are 1,4-butanediol, 1,2-propanediol, 1,10-decanediol and glycol. An appropriate thio compound is, for example, 2-mercaptoethanol.

Appropriate diamines or amino alcohols are primary and secondary aliphatic, cyclo-aliphatic, aliphatic-aromatic and aromatic diamines or amino alcohols, preferably with 2 to 44 carbon atoms. This includes, among others, dimeric fatty acids from natural fats and oils. Additional structural elements or further functional groups, e.g. ether groups, diamide groupings, amino groups, keto groups or sulfone groups, may be arranged between the two amino functions of the diamines in the hydrocarbon chain or attached to the cycloaliphatic or aromatic group. Preferably used diamines are 1,2-diaminoethane, 1,3-diaminopropane, 1,6-diaminohexane, 1,8-diaminooctane, piperazine, diethylenetriamine, 4,7,10-trioxatridecane-1, 13-diamine, 3,3'-diaminodiphenyl sulfone, , 3,3'-dimethyl-4, 4'-diaminodicyclohexylmethane and commercial ether diamines of the following formula:

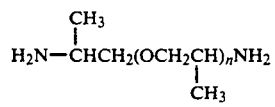

where n is an integer ranging from 1 to 2000. 1,2-diaminoethane and 1,6-diaminohexane are particularly preferred. Preferred amino alcohols are 2-aminoethanol and 3-aminopropanol.

If difatty acid diesters, difatty acid diamides or difatty acid amide esters are to be obtained as reaction products, the diols, diamines and amino alcohols are preferably reacted in stoichiometric mixing ratios, so that a single amino or alcohol group can react per fatty acid carboxylic group. In the case of the diamines, the mixing ratio is not so critical, however, because the monoamide surprisingly forms only when there is a very great excess of amino functions.

Desirable products of the reaction with amino alcohols or diamines include the monofatty acid amides of the said fatty acids, because in such compounds the OH group of amino alcohol or the free amino group of the reacted diamine may act as a second coupling group besides the functional group of the fatty acid, which permits linking the monomers to give polymers. If an excess of amino alcohol is used, monofatty acid amides are obtained almost exclusively because of the higher reactivity of the amino function. As outlined above, monofatty acid amide amines also result when a great excess of diamines is used.

In order to ensure a homogeneous course of reaction, the reaction may also take place in an appropriate solvent. Depending on the kind of reaction to be performed, polar as well as non-polar solvents can be used, particularly methanol, ethanol, propanol, butanol, toluene, xylene or petroleum ether.

The reaction can occur at temperatures between 20° and 300° C., but the temperature range between 50° and 200° C. is preferred, because the reaction times in this temperature range are reasonably short.

As a precaution the reaction is carried out in a closed system, e.g. an autoclave. It requires no complicated procedure, but an inert gas atmosphere, e.g. of argon or nitrogen, or possibly the solvent atmosphere, is preferred because this provides more protection against undesired side-reactions such as oxidation of the initial substances.

If necessary, catalysts such as ammonium chloride or p-toluene-sulfonic acid can be added to the reaction mixture. In addition, it is possible further auxiliary materials and additives such as polymerization inhibitors and antioxidants, e.g. ascorbic acid or glucose.

When the reaction is over, and after the possibly used solvent has been removed, the reaction products can be separated by simple or fractionated crystallization and if necessary, they can be recrystallized from appropriate solvents. Both polar and non-polar substances can be used as solvents for crystallization. Recrystallization is preferably done with methanol or ethanol. A simple washing process is possibly sufficient for obtaining pure reaction products. In specific cases it is advantageous to subject the reaction mixture to a hot vapour extraction process to obtain the reaction products in pure form.

Unless the fatty acids with hydroxyl groups or amino groups were already contained in the natural fats and oils, or if they were produced by oxidation or another kind of reaction of the initial substance, the intermediate products resulting from the above-described method—provided they contain double bonds—can still be turned into appropriate functional compounds either before or after a possible purification step. In this case it is also interesting to form epoxy groups as reactive groups for further reaction.

Monomers that can be obtained according to this method, and that are of special interest for further reaction to give plastics, are in particular the diesters, diamides and amide esters of those derivatives of fatty acids, especially of stearic acid, which contain one or more double bonds, epoxy groups, amino groups or hydroxyl groups as close to the chain end as possible, usually near the carbon atoms 9 to 16. Such derivatives are, for example, oleic acid, ricinoleic acid, 9-1 10- or 12-hydroxystearic acid, 9,10 -epoxystearic acid, linoleic acid, linolenic acid and erucic acid, as well as the mono- and oligohydroxy or mono- and oligoepoxy compounds that can be derived from the said acids, especially 9,10-dihydroxystearic acid. The diesters, diamides and amide esters need not have a symmetrical structure, but may contain different fatty residues. Further interesting substances are the monofatty acid amides of the said substituted acids, which can be obtained by reaction with amino alcohols or diamines.

The monomers that can be obtained according to this method have at least two functional groups of which either both belong to the fatty acid residue, as in the case of the diamides, diols or amide esters, or which come partly from the fatty acid and partly from the amino alcohol or the diamine, as in the case of the monofatty acid amides obtained by reaction with the amino alcohols or diamines. Under the known appropriate conditions, such monomer compounds can be linked with suitable bifunctional compounds to give linear polymers.

According to the invention it is possible, for example, to react with disulphur dichloride the diamides, diesters and amide esters of fatty acids that contain several double bonds in the fatty acid residues, e.g., oleic acid compounds such as dioleic acid ethylenediamide, to give polymers.

Monomers which contain at least two hydroxyl functions or one amino group and one hydroxyl group can be reacted with the diisocyanates that are known in plastics production, for example, hexamethylene diisocyanate, methylenediphenyldiisocyanate (MDI), or the diisocyanates that are available under the trade names Desmodur E14 and T80. Other bifunctional compounds suitable for reacting this momoner class are activated dicarboxylic acids or dicarboxylic acid derivatives such as acid chlorides, esters, anhydrides, azides or nitriles, corresponding thio acids or the diketenes. Preferably used representatives of such bifunctional compounds are phthalic acid dichloride, adipic acid dichloride, maleic acid dichloride or phosgene.

A further very interesting class of polymers is obtained when the epoxy compounds of diamides, diesters or amide esters are reacted with diols, e.g. 1,4-butanediol, or the respective thio compounds. In this case the respective monomers are linked together via ether or thioether groups that are located close to a hydroxyl group. The epoxy compounds can also be linked via dicarboxylic acids or via amino alcohols or diamines.

In the embodiments according to the invention of the diesters, diamides and amide esters, the fatty acids in the monomers are linked head-to-head via the carboxyl group. Especially in the case of the hydroxyl-group-containing diamides combined with diisocyanates as monomer-linking reagents, this is a completely new structural principle of polymers which leads to the novel category of plastics: polyamide urethanes. The kind of linkage results in a particularly strong polar interaction between the polymer chains in this case, without impairing the thermoplastic properties of the plastic material. An example is the reaction of bis-12-hydroxystearic acid-1,2-N,N'-ethylenediamide with hexamethylene diisocyanate. Similarly interesting plastics of the same structure, namely polyamide esters, are obtained when the diisocyanate compound is replaced by activated dicarboxylic acids, e.g. adipic acid dichloride.

The individual components are reacted according to the conventional methods which are used in plastics production -and with which persons skilled in the art are familiar. Related to the functional groups to be reacted, the individual components are introduced in equimolar amounts, and the reaction is performed at a temperature between 20° and 180° C., preferably in the melt and, for precautionary reasons, in an inert gas atmosphere, e.g. of nitrogen.

The special advantage of the method according to the invention consists in the multitude of possibilities of varying the properties of the plastics which this system provides. The properties can be influenced either by the component which links the fatty acids via the carboxyl function, i.e. the diamines, diols or amino alcohols, or by the choice of the fatty acid, and finally by the bifunctional linking component with which the monomers are reacted, e.g. the diisocyanate or the acid dichloride. In addition, it is possible to convert into polymers mixtures of different monomers such as bis-ricinoleic acid-1,2-N,N'-ethylenediamide and bis-ricinoleicacid-1,6-N,N'-hexamethylenediamideorbis-ricinoleic acid-1 2-N,N'-ethylenediamide and bis-12-hydroxystearic acid-1,2-N,N'-ethylenediamide, whereby the resultant plastics properties can be influenced further. Generally speaking, the rules of classical polymer chemistry must be observed in this connection. Thus, it should be noted that the flexibility of the plastics will increase as the chain length increases and that the same is true for the length of the various bifunctional compounds that act as linking elements. As the fatty acids in natural fats and oils, which will probably be mainly used as initial substances for producing the plastics according to the invention, usually carry their functional groups approximately in the middle of the fatty acid chain (ricinoleic acid, for example, carries the OH group at $C_{12}$, and oleic acid carries the double bond between $C_9$ and $C_{10}$), the linked polymer chains always contain more or less long-chained aliphatic residues. Such aliphatic residues in polymers not only render the plastic material hydrophobic but also act as internal plasticizers. Therefore, their presence can be used to advantage for obtaining flexible plastics. Vice versa, the polar types of bonds that may occur in this plastic system may counteract this placticizing effect by hydrogen bridge linkages or by the formation of allophanate or else, this possibly undesired effect of the side chains may be compensated by choosing appropriate bifunctional linking elements. How extremely important these linking elements are due to their variability is best exemplified by the dimers of ricinoleic acid, which can be used only to a limited extent, for example, in polyester production, because of the inevitable plasticising effect of the aliphatic side chains on the backbone of the polymer structure.

Because of the favourable adhesive properties that are associated with it, the polarity of the bonds makes the plastics obtained in this way particularly useful for glass-fibre-reinforced composites, the low processing temperature representing another advantage of this system.

Generally speaking, the described possibilities of variation thus permit plastics to be produced that are perfectly tailored to the respective requirements. For example, it is possible to produce plastic materials which can be processed thermoplastically, used for injection moulding and for extrusion into sheets or films. Other properties such as tensile strength, stretchability, impact strength, softening point or crystallinity can also be varied within wide limits. on the other hand, thermosetting plastics can also be obtained in this way.

Another advantage of the present invention is that the initial fatty acid molecules that are linked via the carboxyl function are already relatively large compared with the monomers that are normally used for the production of plastics; hence, the further reaction with bifunctional reactive compounds needs only comparatively few linkage reactions to give linear polymers of sufficient chain length.

Surprisingly it was also found that plastics with astonishingly good properties can still be obtained even if there is a relatively great portion of chain-terminating compounds among the carboxyl-group-linked fatty acids, i.e. compounds which normally result from the reaction of a fatty acid that contains no functional group in the aliphatic chain, and which therefore have only a single functional group available for further reaction. As, furthermore, compounds without functional groups cannot lead to chain termination but rather behave like normal additives, it may even be superfluous to purify and isolate the resultant monomers if oils and fats are used that have a sufficiently high content of fatty acids with functional groups.

In addition, the carboxyl-linked fatty acid components can also be incorporated in other plastics systems where they may act as plasticizers, for example. Thus, reacting 1,4-butanediol as the alcohol component with hexamethylene diisocyanate yields hard and brittle plastics. If part of the butanediol is replaced in this reaction by bis-12-hydroxystearic acid-1,2-N,N'-ethylenediamide, the resultant plastics are much more flexible and elastic.

As outlined above, the use of fats and oils as initial substance for the plastics industry has been limited so far, because direct use of triglycerides containing fatty acids with appropriate functional groups results only in thermoset plastics, or else, it is necessary to split the fatty acids by oxidation, which involves the loss of a major portion of the available fatty acid material. The invention for the first time provides a method which permits a wide variety of plastics with very different properties or combinations of properties to be produced from fats and oils without prior splitting of the fatty acid residues. What is more, these plastics are in fact polymers that can be obtained, at least in part, from biological sources, so that it can be expected that these products will be easier to decompose and, in the long run, more environmentally compatible than the majority of conventional plastics.

The present invention is exemplified in the following examples:

EXAMPLE 1

Preparation of bis-12-hydroxystearic acid-1,2-N,N'-ethylenediamide 153 g hardened castor oil and 15 g ethylenediamine are stirred for 5 hours in an autoclave in a nitrogen atmosphere at 140° C. The reaction product is recrystallized from hot methanol.

Melting point: 142°–145° C.; yield: 106.5 g

EXAMPLE 2

Preparation of bis-12-hydroxystearic acid-1,6-N,N'-hexamethylene diamide 5.1 g hardened castor oil and 0.97 g hexamethylenediamine are stirred for 5 hours in an autoclave in a nitrogen atmosphere at 150° C. The reaction product is subjected to hot vapour extraction with methanol.

Melting point: 135°–136° C.; yield: 3.7 g

EXAMPLE 3

Preparation of bisricinoleic acid-1,2-N,N'-ethylenediamide 1.5 g castor oil and 0.5 g 1,2-diaminoethane are stirred for 5 hours in a nitrogen atmosphere at 120° C. The product is recrystallized from methanol.

Melting point: 83°–85° C.; yield: 2.6 g

EXAMPLES 4

Reaction of bis-12-hydroxystearic acid-1,2-N,N'-ethylenediamide with hexamethylene diisocyanate 3 g of the product obtained according to Example 1 is melted, in a nitrogen atmosphere and heated up to 155° C. A volume of 0.79 ml hexamethylene diisocyanate is added to this substance and thoroughly stirred. The reaction mixture is kept at 150° C. for 45 minutes and then cooled down to room temperature. The resultant polyurethane amide is thermoplastic.

EXAMPLE 5

Reaction of bis-12-hydroxystearic acid-1,2-N,N'-ethylenediamide with Desmodur E14

0.83 g bis-12-hydroxystearic acid-1,2-N,N'-ethylenediamide and 3.22 g Desmodur E14 are kept for 2 hours in a nitrogen atmosphere at 150° C. The resultant product is thermoplastic.

EXAMPLE 6

Reaction of bis-12-hydroxystearic acid-1,6-N,N'-hexamethylenediamide hexamethylenediamide with Desmodur T80

6.8 g bis-12-hydroxystearic acid-1,6-N,N'-hexamethylenediamide is melted and heated up to 160° C. in a nitrogen atmosphere. 1.74 g Desmodur T80 (aromatic diisocyanate) is added. Then the reaction mixture is kept for 4 hours at 160° C. The resultant polyurethane amide is thermoplastic.

EXAMPLE 7

Reaction of bisricinoleic acid-1,2-N,N'-ethylenediamide with hexamethylene diisocyanate 2.00 g bisricinoleic acid-1,2-N,N'-ethylenediamide is melted and heated up to 100° C. in a nitrogen atmosphere. Then 0.54 g hexamethylene diisocyanate is added. The solution is kept at 100° C. for 4 hours. The resultant plastic can be pressed into sheets or films at 110° C.

EXAMPLE 8

Reaction of bis-12-hydroxystearic acid-1,2-N,N'-ethylenediamide with 1,4-butanediol and hexamethylene diisocyanate 2.45 g of the product obtained according to Example 1 and 0.54 g 1,4-butanediol is heated up to 150° C. In a nitrogen atmosphere, 1.68 g hexamethylene diisocyanate is added. The reaction mixture is kept at 150° C. for 1 hour. The resultant polyamide urethane is thermoplastic and stretchable. This polyamide urethane is pressed into a film at 200° C. The film is placed between two glass plates. The glass plates are heated up to 190° C. and slightly pressed together. After cooling, the two glass plates are tightly bonded.

EXAMPLE 9

Reaction of bis-12-hydroxystearic acid-1,2-N,N'-ethylenediamide with 1,10-decanediol and hexamethylene diisocyanate 1.88 g bis-12-hydroxystearic acid-1,2-N,N'-ethylenediamide and 0.35 g 1,10-decanediol are heated up to 145° C. Then, 0.84 g hexamethylene diisocyanate is added in a nitrogen atmosphere. The reaction mixture is kept at 145° C. for 35 minutes. The resultant polyamide urethane is thermoplastic and stretchable.

EXAMPLE 10

30 g bis-12-hydroxystearic acid-1,2-N,N'-ethylenediamide, 120 ml 6 N sodium hydroxide solution and 350 ml methanol are stirred for 5 hours in an autoclave in a nitrogen atmosphere at 180° C. The methanol is drawn off, and the residual product is dried over $P_4O_{10}$. The dried product is poured into boiling 2 N $H_2SO_4$ and stirred for 2 hours. After cooling to room temperature, the wax-like product is dissolved in chloroform. The chloroform phase is twice extracted with water and then dried. Subsequently, the chloroform is drawn off and 12-hydroxystearic acid is obtained.

EXAMPLE 11

0.60 g 12-hydroxystearic acid and 0.34 g hexamethylene diisocyanate are heated up to 150° C. Foaming occurs at once. The foam is stable and elastic.

It will be understood that the above description of the present invention is susceptible to various modifications, changes and adaptations, and the same are intended to be comprehended within the meaning and range of equivalents of the appended claims.

We claim:

1. A thermoplastic linear polymer obtained by a process of preparing and reacting a monomer containing two reactive groups comprising steps for:
   (a) reacting at least one natural fatty acid or ester selected from the group consisting of unsaturated fatty acids or esters and hydroxyl-group containing fatty acids or esters with an equimolar amount of a bifunctional ester- or amide-forming compound to produce a monomer component, comprising at least one difatty acid diamide, difatty acid diester, difatty acid amide ester, monofatty acid amide amine or monofatty acid amide alcohol, having only two groups reactive with a second bifunctional compound to produce a thermoplastic linear polymer said reactive groups including ethylenic double bonds, hydroxyl groups, epoxy groups or amino groups; and
   (b) subsequently reacting said monomer component with an equimolar amount of said second bifunctional compound selected from the group consisting of disulfur dichloride, diisocyanate, dicarboxylic acid and activated dicarboxylic acid.

2. The thermoplastic polymer as set forth in claim 1, wherein said natural fatty acids or esters comprise unsaturated hydroxyl-group-containing fatty acids or fats and oils with unsaturated hydroxyl-group-containing fatty acids in their fatty acid composition.

3. The polymer as set forth in claim 1, wherein said fatty acids or esters comprise euphorbia oil, olive oil, linseed oil, caster oil or hydrogenated caster oil, sunflower oil, rapeseed oil, oil of Jatropha curcas, or oil from seeds of Euphorbia lathyris.

4. The thermoplastic polymer as set forth in claim 1, wherein said amide-forming bifunctional compound comprises an aliphatic, cycloaliphatic, aliphatic-aromatic or aromatic diamine.

5. The thermoplastic polymer as set forth in claim 1, wherein said amide-forming bifunctional compound comprises an 1,2-diaminoethane or 1,6-diaminohexane.

6. The thermoplastic polymer as set forth in claim 1, including an ester-forming and amide-forming bifunctional compound comprising an aliphatic, cycloaliphatic, aliphatic-aromatic or aromatic amino alcohol.

7. The thermoplastic polymer as set forth in claim 6, wherein said ester-forming and amide-forming bifunctional compound is 2-aminoethanol or 3-aminopropanol.

8. The thermoplastic polymer as set forth in claim 1, wherein the reaction with ester-forming or amide-forming bifunctional compound is carried out at temperatures between about 20° and 300° C.

9. The thermoplastic polymer as set forth in claim 8, wherein the reaction with ester-forming or amide-forming bifunctional compound is carried out at temperatures between about 50° and 200° C.

10. The thermoplastic linear polymer set forth in claim 1, wherein said second bifunctional compound is disulfur dichloride.

11. The thermoplastic linear polymer set forth in claim 1, wherein said second bifunctional compound is a diisocyanate.

12. The thermoplastic linear polymer set forth in claim 1, wherein said second bifunctional compound is a dicarboxylic acid.

13. The thermoplastic linear polymer set forth in claim 1, wherein said second bifunctional compound is an activated dicarboxylic acid.

14. The process for preparing a thermoplastic linear polymer set froth in claim 1, wherein said natural fatty acid or ester in step (a) is an unsaturated fatty acid or ester without hydroxyl groups.

15. The process for preparing a thermoplastic linear polymer set forth in claim 14, including first reacting said unsaturated fatty acid or ester to obtain a hydroxyl-group containing fatty acid or ester and then reacting said hydroxyl-group containing fatty acid or ester to yield at least one difatty acid diamide, difatty acid diester, difatty acid amide ester, monofatty acid amide amine or monofatty acid amine alcohol.

* * * * *

UNITED STATES PATENT AND TRADEMARK OFFICE
CERTIFICATE OF CORRECTION

PATENT NO. : 5,302,670
DATED : April 12, 1994
INVENTOR(S) : Rainer FRISCHE et al.

It is certified that error appears in the above-indentified patent and that said Letters Patent is hereby corrected as shown below:

the title page, Item [30], Foreign Application Priority Data, to read --

June 29, 1989 [DE]  Fed. Rep. of Germany 3921306.4  -- .

Signed and Sealed this

Fifth Day of May, 1998

Attest:

BRUCE LEHMAN

*Attesting Officer*    *Commissioner of Patents and Trademarks*